United States Patent [19]

Blum et al.

[11] 4,415,499

[45] Nov. 15, 1983

[54] PROCESS FOR THE MANUFACTURE OF PALLADIUM(II) CATALYST AND FOR THE MANUFACTURE OF ALKENYL ESTERS OF CARBOXYLIC ACIDS EMPLOYING SAID CATALYST

[75] Inventors: Klaus Blum; Rudolf Strasser, both of Burghausen, Fed. Rep. of Germany

[73] Assignee: Wacker-Chemie GmbH, Munich, Fed. Rep. of Germany

[21] Appl. No.: 309,006

[22] Filed: Oct. 6, 1981

[30] Foreign Application Priority Data

Dec. 16, 1980 [DE] Fed. Rep. of Germany ....... 3047347

[51] Int. Cl.$^3$ .............................................. C11C 3/02
[52] U.S. Cl. ............................ 260/410.9 N; 252/446; 560/113; 560/234; 560/261; 502/180
[58] Field of Search ................ 260/410.9 N; 252/446; 560/113, 234, 261

[56] References Cited

U.S. PATENT DOCUMENTS

| | | | |
|---|---|---|---|
| 2,347,955 | 5/1944 | Korpi | 252/446 X |
| 2,600,379 | 6/1952 | Doumani et al. | 252/446 |
| 3,188,319 | 6/1965 | Smidt et al. | 260/410.9 N X |
| 3,658,724 | 4/1972 | Stiles | 252/446 |
| 3,755,387 | 8/1973 | Young | 260/410.9 N |
| 4,052,335 | 10/1977 | Michalczyk et al. | 252/446 |
| 4,310,709 | 1/1982 | Rebafka | 560/113 X |

*Primary Examiner*—Helen M. S. Sneed
*Attorney, Agent, or Firm*—Allison C. Collard; Thomas M. Galgano

[57] ABSTRACT

The invention relates to supported catalysts based on a palladium(II) salt and activated carbon, there being used, as the support material, activated carbon having an analytical SiO$_2$ content of from 0.5 to 8% by weight. The catalysts according to the invention are used for reacting carboxylic acids with alkenyl esters of lower carboxylic acids.

4 Claims, No Drawings

PROCESS FOR THE MANUFACTURE OF PALLADIUM(II) CATALYST AND FOR THE MANUFACTURE OF ALKENYL ESTERS OF CARBOXYLIC ACIDS EMPLOYING SAID CATALYST

The invention relates to palladium(II) catalysts, and their manufacture and use.

Palladium(II) salt catalysts with activated carbon as their support material are known per se. For example, according to CA 69, 1968, 58799 h, a catalyst of this type is proposed for the vinylation of propionic acid with vinyl acetate. A service life of at least 250 hours is indicated. The activity of that catalyst, however, is too short for industrial use if the given dwell time of the reaction mixture of from 3 to 3.5 hours is taken into consideration.

Furthermore, DE-PS No. 11 27 888 describes palladium(II) salt catalysts for the manufacture of vinyl esters of higher carboxylic acids, with activated carbon again being recommended as the support material. A disadvantage of catalysts of this type is their short service life: after an operating period of only approximately 100 hours, conversion losses of approximately 10% must be accepted. Furthermore, even after a very short operating period (approximately 20 hours) losses of the palladium salt occur.

It is therefore the object of the present invention to provide palladium(II) salt catalysts having an increased useful life.

It has now been found that this object can be attained by using, as a support material for the palladium(II) salt catalyst, activated carbon having an analytical $SiO_2$ content of at least 0.5% by weight.

The present invention provides a supported catalyst based on a palladium(II) salt and activated carbon which is characterized in that the support material is activated carbon having an analytical $SiO_2$ content of from 0.5 to 8% by weight. The $SiO_2$ content is preferably in the range of from 0.8 to 5.0% by weight.

The palladium content of the supported catalysts according to the invention is within the limits known per se. Excellent results are achieved with a palladium content of from 2 to 4% by weight, based on the total weight of the catalyst.

Advantageously, double salts of palladium(II) are used, at least partially, as palladium(II) salts for the catalyst according to the invention. There comes into consideration, as additional components for these double salts, the salts of alkali metals, especially lithium, sodium, and potassium; of alkaline earth metals, for example, magnesium, calcium, and barium; and of rare earth metals, for example, neodymium, cerium, lanthanum and dysprosium.

Activated carbon having an analytical $SiO_2$ content of from 0.5 to 8% by weight is commercially available. It can be prepared, for example, using, as starting material, activated carbon containing little or no $SiO_2$, by impregnating the material with water glass and the like and subsequently heating the impregnated material. The activated carbon to be used according to the invention can, however, be obtained also, for example, from mineral coals having a corresponding $SiO_2$ content, after they have been converted into activated carbon in a manner known per se by thermal treatment.

The analytical $SiO_2$ content of the activated carbon is determined, in the usual manner, after burning the material.

The catalysts according to the invention are prepared by impregnating the corresponding support material with a palladium(II) salt solution.

A preferred manufacturing process is characterized in that activated carbon having an analytical $SiO_2$ content of from 0.5 to 8% by weight is impregnated with a palladium(II) solution having a pH of from 1 to 6 and, preferably, from 2 to 5.

The term "impregnation" is to be understood as meaning the treatment of activated carbon with a palladium(II) solution carried out in such a manner that palladium(II) is absorbed by the activated carbon. This is carried out, for example, by shaking a suspension of activated carbon in a palladium(II) salt solution, by stirring such a suspension, by allowing such a suspension to stand, or by a like method.

In general, there is used, as starting material, a solution of $Pd(II)Cl_2$ in strong hydrochloric acid adjusted to a pH of from 1 to 6 by the addition of a base. As bases, there comes into consideration, above all, the oxides and hydroxides of alkali metals, alkaline earth metals, and rare earth metals. This enables the additional components of the palladium double salt to be introduced in a simple manner. In principal, however, such additional components may alternatively be introduced in the form of, for example, neutral salts.

Furthermore, the adsorption of the salt components by the active carbon can be aided by the addition of organic compounds, such as acetone and the like, to the Pd(II) salt solution.

The catalysts according to the invention are superior to conventional palladium(II) salt/activated carbon catalysts in their increased service life. The losses of palladium(II) salt, known according to the prior art, are miminal even with relatively long operating times.

The catalysts according to the invention promote the alkenylation of carboxylic acids by alkenyl esters of lower carboxylic acids.

The present invention therefore also provides a process for the manufacture of alkenyl esters of carboxylic acids by reacting carboxylic acids with alkenyl esters of lower carboxylic acids, characterized in that supported catalysts based on a palladium(II) salt and activated carbon are used, the activated carbon having an analytical $SiO_2$ content of from 0.5 to 8% by weight.

The alkenylation reactions are generally carried out at the pressure of the surrounding atmosphere and at temperatures of from 40° to 100° C.

Since equilibrium reactions are involved, the alkenylation agent is advantageously added in excess. The molar ratio of the alkenyl carboxylate to the carboxylic acid is from 1:1 to 5:1, preferably approximately 3:1. As alkenylation agents, there are used alkenyl esters of lower carboxylic acids. Examples of these are, inter alia, vinyl acetate, allyl acetate, methallyl acetate, propenyl acetate, isopropenyl acetate, vinyl propionate and, especially, vinyl acetate.

Examples of carboxylic acids are propionic acid, butyric acid, valeric acid, caprylic acid, capric acid, lauric acid, palmitic acid, stearic acid, crotonic acid, sorbic acid, oleic acid, cyclohexanecarboxylic acid, benzoic acid, pivalic acid, α-chloropropionic acid, adipic acid, and caproic acid.

The reaction may be continuous or discontinuous. A continuous manner of working is carried out, for example, in a heatable column arrangement, analogous to an arrangement for column chromatography, in which the dwell time of the reactants can be controlled by the feed and discharge rates of the reaction mixture.

By means of the processes of the invention, it is possible to carry out the alkenylation of carboxylic acids with high space/time yields.

The invention is explained in detail below with reference to the following examples which are given by way of illustration and not of limitation.

EXAMPLE 1

Manufacture of the catalyst 1.16 g of palladium chloride are dissolved in 2 ml of concentrated hydrochloric acid and diluted with 30 ml of distilled water. The solution is adjusted to pH 3 by adding 11.4 ml of 1N NaOH. 30 ml of acetone are then added. 20 g of granular activated carbon having an analytical $SiO_2$ content of 0.9% by weight are then suspended in the solution thus obtained. After approximately 10 minutes, the solution becomes discolored. The activated carbon impregnated in that manner with a palladium(II) salt is then filtered off, and finally dried at 80° C. in a nitrogen stream.

EXAMPLE 2

1.16 g of $PdCl_2$ and 1.8 g of $NdCl_3$ are dissolved in 3.5 ml of concentrated hydrochloric acid and 11.5 ml of 1N NaOH are added. The solution has a pH of 2.0. Finally, 30 ml of acetone are added.

20 g of granular activated carbon having an analytical $SiO_2$ content of 0.9% by weight are then treated with the solution thus prepared in a manner analogous to that described in Example 1.

EXAMPLE 3

The method according to Example 1 is repeated, except that granular activated carbon having an analytical $SiO_2$ content of 2.0% by weight is used.

EXAMPLE 4

The method according to Example 3 is repeated, except that the solution is adjusted to pH 5 with KOH, instead of to pH 3 with NaOH.

EXAMPLE 5

The method according to Example 1 is repeated, except that granular activated carbon having an analytical $SiO_2$ content of 4.9% by weight is used.

Comparison Example 1

The method according to Example 1 is repeated, except that granular activated carbon having an analytical $SiO_2$ content of 0.15% by weight is used.

Comparison Example 2

The method according to Example 3 is repeated, except that, instead of NaOH, 0.66 g of NaCl is used and the pH is less than 0.

EXAMPLE 6

20 g of the catalyst prepared according to Example 1 are introduced into a heatable column. The temperature within the column is maintained at 62° C. A pre-heated mixture of vinyl acetate and lauric acid in a molar ratio of 3:1 is continuously added from a dropping funnel fitted onto the column, and the reaction mixture leaving the column is drawn off, analogously to column chromatography, in such a manner that the dwell time of the reaction mixture within the catalyst zone is 46 minutes.

The conversion to vinyl laurate, based on the lauric acid used, was initially 71%; after a service life of 700 hours, it was 55%; and after 1080 hours, it was still 41%. Accordingly, after a catalyst service life of 1080 hours, there is an average conversion of 57%.

EXAMPLE 7

The method according to Example 6 is repeated, except that the catalyst according to Example 5 is used.

The conversion to vinyl laurate, based on the quantity of lauric acid reacted, was initially 72%; after 600 hours, it was 60%; and after 1160 hours, it was still 41%. Accordingly, with an operating period of 1160 hours, there is an average conversion of 59%.

EXAMPLE 8

The method according to Example 6 is repeated, except that the catalyst according to Example 3 is used.

The dwell time of the reaction mixture within the catalyst zone was 42 minutes. The conversion after 600 hours was still 70%; and after 1240 hours, it was still 40%. Accordingly, with a service life of 1240 hours, there is an average conversion of 63.5%.

EXAMPLE 9

The method according to Example 6 is repeated, except that the catalyst according to Example 2 is used.

The average conversion after 858 hours was 58%.

Comparison Example 3

The method according to Example 6 is repeated, except that the catalyst according to Comparison Example 1 is used.

The average conversion of vinyl laurate, based on the lauric acid used, was 35% after 67 hours.

Comparison Example 4

The method according to Example 6 is repeated, except that the catalyst according to Comparison Example 2 is used.

The conversion to vinyl laurate fell from an initial value of 75%, to 60% after 263 hours, and to 41% after 890 hours.

The overall efficiency of the catalyst was thus only approximately 77% of that of the catalyst according to Example 3.

EXAMPLE 10

The catalyst according to Example 4 is used.

A mixture consisting of 2 parts of vinyl acetate and 1 part of caproic acid is conveyed over the contact material in a manner analogous to that of Example 6, with a dwell time of 43 minutes.

The conversion to vinyl acetate caproate remained constant at 45% over 450 hours. After that period of service, the catalyst was still fully active.

EXAMPLE 11

The catalyst used is analogous to that of Example 3 with an $SiO_2$ content of 2.0% by weight, except that, during the manufacturing process, the solution was adjusted to pH 3 with 1N KOH instead of with 1N NaOH.

Vinyl acetate and caproic acid were reacted, in a molar ratio of 2:1, at 62° C. in the arrangement described according to Example 6, with a dwell time of 42 minutes.

The conversion of caproic acid to vinyl caproate was 53%.

EXAMPLE 12

3 moles of vinyl acetate and 1 mole of benzoic acid are boiled under reflux at 100° C. for one hour in the presence of 20 g of the catalyst according to Example 3.

The conversion of benzoic acid to vinyl benzoate was 58%.

After separation from the reaction mixture, the catalyst was not impaired and could be used again.

Thus, while only several examples of the present invention have been described, it will be obvious that many changes and modifications may be made thereunto, without departing from the spirit and scope of the invention.

What is claimed is:

1. In a process for the manufacture of alkenyl esters of carboxylic acids, the improvement comprising:
   reacting a carboxylic acid with an alkenyl ester of a lower carboxylic acid, in the presence of a supported catalyst comprising a support material comprising activated carbon having an analytical $SiO_2$ content of from 0.5 to 8% by weight and a catalyst impregnated in said support material comprising a palladium(II) salt.

2. The process according to claim 1, wherein said $SiO_2$ content is from 0.8 to 5% by weight.

3. The process according to claim 1, wherein said palladium(II) content is from 2 to 4% by weight, based on the total weight of said catalyst.

4. The process according to claim 1, wherein said reacting step is carried out at a temperature of from 40°–100° C. at atmospheric pressure.

* * * * *